US005997546A

United States Patent [19]

Foster et al.

[11] Patent Number: 5,997,546

[45] Date of Patent: Dec. 7, 1999

[54] GASTRIC BALLOON CATHETER WITH IMPROVED BALLOON ORIENTATION

[75] Inventors: Mark Foster, Sandy, Utah; Allan F. Willis, Chubuck; Kelly J. Christian, Pocatello, both of Id.

[73] Assignee: Ballard Medical Products, Salt Lake City, Utah

[21] Appl. No.: 09/226,173

[22] Filed: Jan. 7, 1999

[51] Int. Cl.$^{6}$ .................................................. A61M 31/00

[52] U.S. Cl. ............................................ 606/108; 604/96

[58] Field of Search .................................... 606/103, 194; 604/96, 101, 102, 97, 103

[56] References Cited

U.S. PATENT DOCUMENTS

| | | | |
|---|---|---|---|
| Re. 35,312 | 8/1996 | Christoudias | 600/207 |
| 3,050,066 | 8/1962 | Koehn . | |
| 4,509,514 | 4/1985 | Brain | 128/207.15 |
| 4,848,343 | 7/1989 | Wallsten et al. | 128/343 |
| 4,927,412 | 5/1990 | Menasche . | |
| 5,074,845 | 12/1991 | Miraki et al. . | |
| 5,154,725 | 10/1992 | Leopold . | |
| 5,171,222 | 12/1992 | Euteneuer et al. . | |
| 5,226,889 | 7/1993 | Sheiban | 604/101 |
| 5,250,040 | 10/1993 | Parks et al. | 604/283 |
| 5,261,879 | 11/1993 | Brill . | |
| 5,308,325 | 5/1994 | Quinn et al. . | |
| 5,330,499 | 7/1994 | Kanesaka . | |
| 5,334,143 | 8/1994 | Carroll . | |
| 5,395,335 | 3/1995 | Jang . | |
| 5,807,331 | 9/1998 | Den Heijer et al. | 604/101 |
| 5,836,924 | 11/1998 | Kelliher et al. | 604/248 |
| 5,865,816 | 2/1999 | Quinn | 604/280 |
| 5,876,344 | 3/1999 | Baker et al. | 600/463 |
| 5,891,027 | 4/1999 | Tu et al. | 600/374 |

FOREIGN PATENT DOCUMENTS

| | | | |
|---|---|---|---|
| 4028466 | 3/1992 | Germany | 604/96 |
| 3105883 | 8/1992 | Germany | 604/96 |

*Primary Examiner*—Paul J. Hirsch
*Assistant Examiner*—Michael B. Priddy
*Attorney, Agent, or Firm*—Morriss Bateman O'Bryant & Compagni

[57] ABSTRACT

A balloon catheter with improved balloon orientation includes a head, a catheter segment extending from the head, and a balloon disposed on the catheter segment opposite the head. Preferably, the balloon is attached to the exterior of the catheter segment at a proximal location and to the interior of the catheter segment at a distal location to thereby form a balloon which extends distally from the distal end of the catheter segment when inflated. The improved orientation of the balloon helps to prevent contact between the distal end of the catheter segment and anatomical structures of the user, thereby reducing irritation.

25 Claims, 3 Drawing Sheets

GASTRIC BALLOON CATHETER WITH IMPROVED BALLOON ORIENTATION

BACKGROUND OF THE INVENTION

1. Field of the Invention

The present invention relates generally to balloon catheters which are used for catheterizing a body cavity. More specifically, the present invention relates to a balloon catheter with an improved balloon orientation wherein the balloon is configured to decrease irritation caused by the catheter while the catheter remains in the body cavity.

2. State of the Art

There are numerous situations in which a body cavity must be catheterized to achieve some desired medical goal. Most frequently, catheterization is performed either to insert substances into or to remove substances from the body. During many of these procedures, it is necessary to keep the catheter in a relatively stable position to perform the desired insertion or removal. With the use of enteral feeding catheters (i.e. catheters which enable the administration of nutritional solutions directly into the stomach or intestines), for example, it is necessary to ensure that the catheter is not accidentally removed from the stomach or intestines. This is true both during the actual administration or removal of fluids, and the time periods in between feedings.

In order to ensure that a catheter is maintained in the proper position, it is common to use a balloon disposed near the distal (patient) end of the catheter shaft. Inflating the balloon causes the balloon to contact the anatomical structure (i.e. a duct or stomach wall) and thereby prevents the catheter from moving out of the proper position. In the case of enteral feeding, a stoma is formed leading into the stomach or intestine. A catheter is positioned to extend through the stoma, so as to form a channel into the stomach or intestines through which enteral feeding solutions may be pumped.

FIG. 1 shows a side view of a balloon catheter, generally indicated at 10, made in accordance with the prior art. The balloon catheter 10, has a head 14 disposed at a proximal end. The head 14 contains valves which regulate the flow of fluids through the balloon catheter 10. The head 14 also prevents the balloon catheter 10 from completely advancing through the stoma and into the stomach or intestine of the user.

To prevent the catheter from being pulled out of the stomach/intestinal wall, a balloon 18 is disposed along a catheter segment 22. The catheter segment 22 includes an elongate catheter shaft 26 and a stiff tip 30 which is attached to the catheter shaft at a distal end opposite the head 14. The catheter shaft 26 is typically made of a medical grade silicone. The stiff tip 30 is also typically formed of a medical grade silicone, but is usually configured to be more rigid than the catheter shaft. The stiff tip 30 assists the physician, etc., in inserting the catheter segment 22 through the stoma.

The balloon 18 is typically attached at a proximal end 18*a* to the catheter shaft 26 by the use of adhesive, thereby forming a proximal cuff 32. Likewise, the distal end 18*b* of the balloon 18 is typically adhesively attached to the stiff tip 30, thereby forming a distal cuff 34.

The balloon 18 is advantageous because it allows the catheter segment 22 to be inserted into the stoma while the balloon is uninflated. Once the catheter segment 22 is properly positioned in the stoma, a syringe (not shown) is inserted into a side port 36 of the head 14 and a fluid is injected into the balloon 18 through a lumen (not shown in FIG. 1) of the catheter. The fluid inflates the balloon so that it extends outwardly from the catheter shaft 26 and the stiff tip 30.

While the balloon 18 remains inflated, the catheter segment 22 stays properly positioned in the stoma. If the catheter segment 22 needs to be removed, the balloon 18 may be deflated so that it will not interfere with withdrawal of the catheter shaft 26 and stiff tip 30. In such a manner, the position of the balloon catheter 10 is maintained until removal is desired.

While the configuration shown in FIG. 1 works well for maintaining the balloon catheter 10 in the proper position, the balloon catheter does have disadvantages. A primary disadvantage is discomfort to the user. In order to allow insertion of the catheter segment 22, the catheter shaft 26 and especially the stiff tip 30 must be relatively firm to prevent buckling under insertion pressures. This same firmness, however, makes the distal tip 26 much more prone to irritate anatomical structures which come into contact with the stiff tip 30. This is especially true in the stomach and intestines where the opposing walls of the anatomical structures tend to collapse on each other during physical exertion, or when the cavity has little or no food. As the person moves, the stiff tip 30 repeatedly engages the adjacent anatomical structure (such as the stomach wall) and can lead to considerable irritation and discomfort for the user.

While it would be advantageous to prevent the stiff tip 30 from contacting any adjacent anatomical structures, the balloon 18 provides certain inherent limitations. The balloon 18 must have the proximal and distal cuffs, 32 and 34, to seal form the balloon when fluid is injected into the lumen in communication with the balloon. Additionally, the cuffs 32 and 34 must be of sufficient length to provide a tight and durable seal between the balloon 18 and the catheter shaft 22 which will withstand bending and flexing caused by movements of the user. Thus, several millimeters of the distal tip 26 (and potentially the distal end of the cuff) are left exposed—leaving a significant potential for irritation.

Another disadvantage with the configuration shown in FIG. 1 is that the distal cuff 34 forms a joint 34*a* at its distal end. The joint 34*a* provides an abrupt edge which has a tendency to catch on the tissue defining the stoma through which the catheter segment 22 is placed, thereby frustrating insertion of the balloon catheter 10. As the joint 34*a* catches on the tissue, it can cause the catheter segment to buckle and can also cause irritation.

Thus, there is a need for an improved balloon catheter having a balloon orientation which isolates the firm distal tip from internal body cavity surfaces. There is also a need for an improved balloon catheter which lacks a joint or abrupt edge along the catheter segment which can interfere with catheter placement through the stoma.

SUMMARY OF THE INVENTION

Accordingly, it is an object of the present invention to provide a balloon catheter having an improved balloon orientation which decreases or eliminates contact between the stiff tip at the distal end of the catheter segment and anatomical structures during use.

It is another object of the present invention to provide such a balloon which is relatively inexpensive to manufacture and relatively easy to use.

It is still another object of the present invention to provide such a balloon catheter which does not obstruct flow of solution through the catheter segment.

It is yet another object of the present invention to provide such a balloon catheter, wherein the balloon catheter does not interfere with the catheter tip upon insertion.

It is still yet another object of the present invention to provide such a balloon catheter which provides a reduced profile lacking joints along the exterior of the catheter segment distal from the proximal cuff to thereby ease insertion of the catheter segment and balloon through the stoma.

The above and other objects of the invention not expressly enumerated are realized in a representative illustrated embodiment of a balloon catheter with improved orientation including an elongate catheter shaft and a stiff tip to aid insertion through a stoma or other opening to a body cavity. Disposed at the distal end of the catheter shaft and at the stiff tip, is a balloon disposed in a coaxial relationship with the catheter shaft and the stiff tip. The balloon is configured to inflate in such a manner that the balloon covers the distal stiff tip and thereby isolates it from adjacent anatomical structures when the balloon catheter is being used.

In accordance with one aspect of the invention, the balloon has a proximal cuff whereat the proximal end of the balloon is attached to the catheter shaft in a sealing engagement. Typically, this is accomplished by the use of a glue. The distal end of the balloon extends over the stiff tip of the catheter to thereby prevent direct contact between the catheter tip and anatomical structures. In a preferred embodiment, the distal end of the balloon extends around the stiff tip and then extends proximally into an opening in the stiff tip to form an attachment cuff within the stiff tip. In such a configuration, the balloon is configured to extend outwardly and slightly distally from the stiff tip upon inflation, thereby preventing contact between the stiff tip and adjacent anatomical structures during use. Additionally, having the balloon stretch over the stiff tip of the catheter provides an elastic buffer between the stiff tip and stoma during insertion of the catheter.

In accordance with another aspect of the invention, the balloon is formed from an elastomeric sleeve which has an inner diameter which is substantially the same as the exterior diameter of the catheter segment. Thus, when the balloon is not inflated, the elastomeric material of the catheter hugs the exterior of the catheter segment, thereby minimizing the size of stoma necessary to comfortably insert the device.

In accordance with still another aspect of the invention, the stiff tip is formed with an annular groove or recess adjacent its distal end. The annular recess is preferably slightly deeper than the thickness of the material forming the balloon. The distal end of the balloon is then adhesively attached to the stiff tip in the annular recess so that the cuff formed by the attachment forms a channel which is approximately the same cross-sectional size as the channel through the remainder of the stiff tip. Preferably, the channel defined by the cuff will be equal to or larger in internal diameter than that running through the remainder of the stiff tip. By providing a cuff which has a channel of substantially the same internal diameter as the remainder of the stiff tip, the cuff does not serve as a restriction to fluid flow through the balloon catheter.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 2:
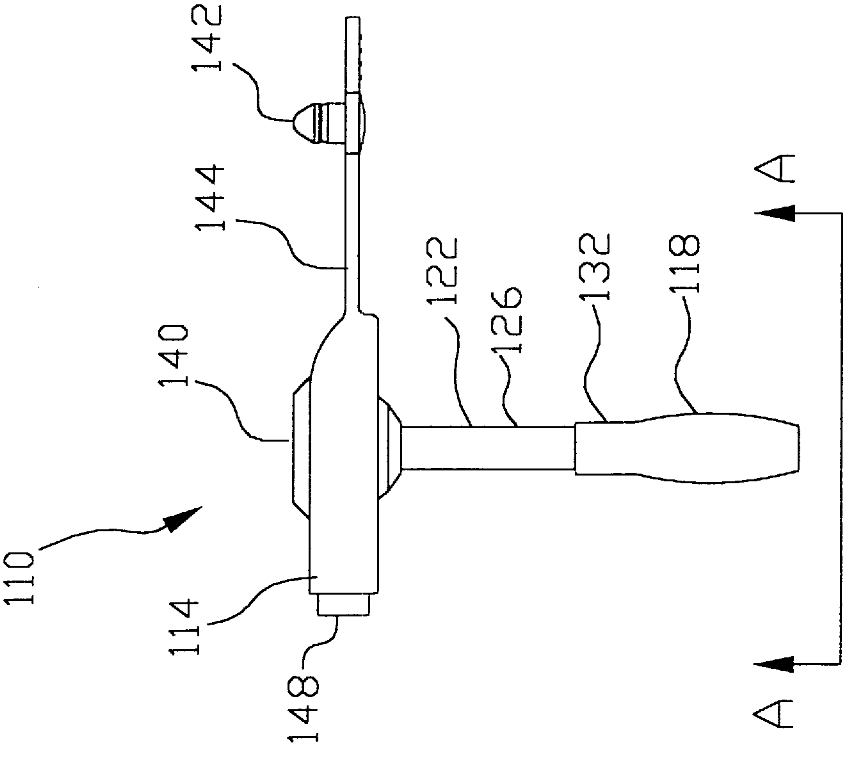
FIG. 2 shows a side view of a balloon catheter made in accordance with the teachings of the present invention, the balloon of the balloon catheter being disposed about the exterior of the catheter segment in an uninflated configuration.

Referring to FIG. 2, there is shown a side view of a balloon catheter, generally indicated at 110, made in accordance with the teachings of the present invention. The balloon catheter 110 is similar to the prior art in that it includes a head 114, an elastomeric sleeve forming a balloon 118, and a catheter segment 122. The catheter segment 122 includes a catheter shaft 126 and a stiff tip (not visible due to the balloon 118) which is attached at a distal end of the catheter shaft. A first, central opening 140 in the head 114 enables the injection of enteral feeding solution, etc., through the catheter segment 122 and into the user. A plug 142 is disposed on a lanyard 144 which extends from the head 114. The plug 142 can be placed in the first, central opening 140 to prevent contamination of the catheter 110 when the opening is not being used to administer fluids through the balloon catheter 110.

A second, side opening 148 serves as a port through which fluid may be injected into or removed from the balloon 118 through a lumen in the catheter segment 122. Thus, the second, side opening 148 enables the user or a physician, etc., to selectively control inflation and deflation of the balloon 118. The specific details of both the first, central opening 140 and the second, side opening 148 are discussed in additional detail in the discussion regarding the cross-sectional view shown in FIG. 3.

Figure 1:
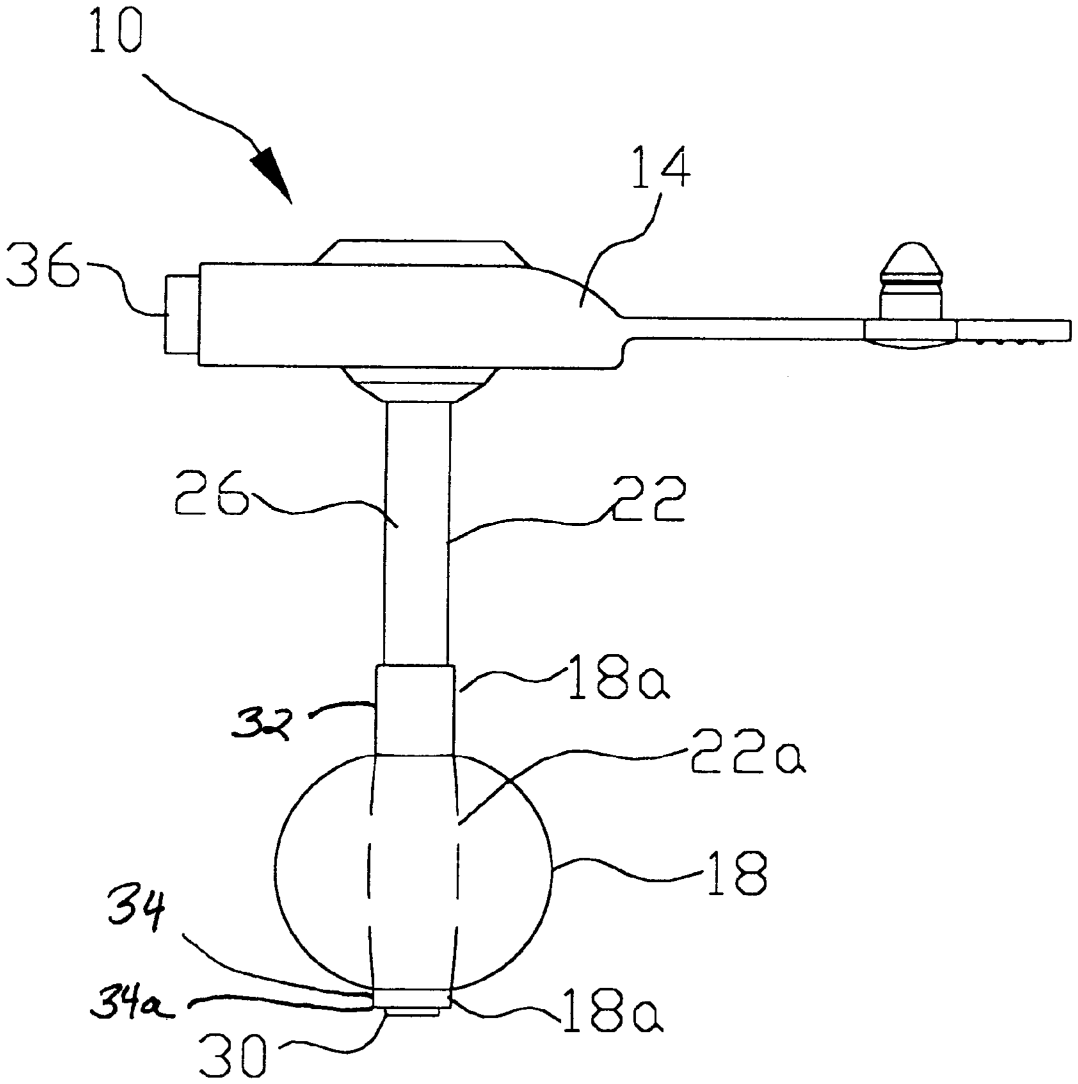
FIG 1 (PRIOR ART)
FIG. 1 shows a side view of a balloon catheter made in accordance with the teachings of the prior art, the balloon catheter being in an inflated configuration.

Like the prior art balloon catheter 10 shown in FIG. 1, the balloon 118 includes a proximal cuff 132 which extends longitudinally along the catheter shaft 126 so as to be coaxial therewith. The balloon catheter 110 also includes a distal cuff (not shown in FIG. 2) which secures the distal end of the balloon 118. However, unlike the prior art balloon catheter 10 of FIG. 1, the distal cuff is not positioned along the exterior of stiff tip, several millimeters proximally of the distal end of the stiff tip. Rather, the distal cuff of the balloon 118 is disposed in such a manner that the balloon covers the distal end of the stiff tip, thereby preventing contact between the stiff tip and anatomical structures adjacent thereto. In such a configuration, the balloon 118 minimizes irritation associated with prior art gastric balloon catheters.

Figure 3:
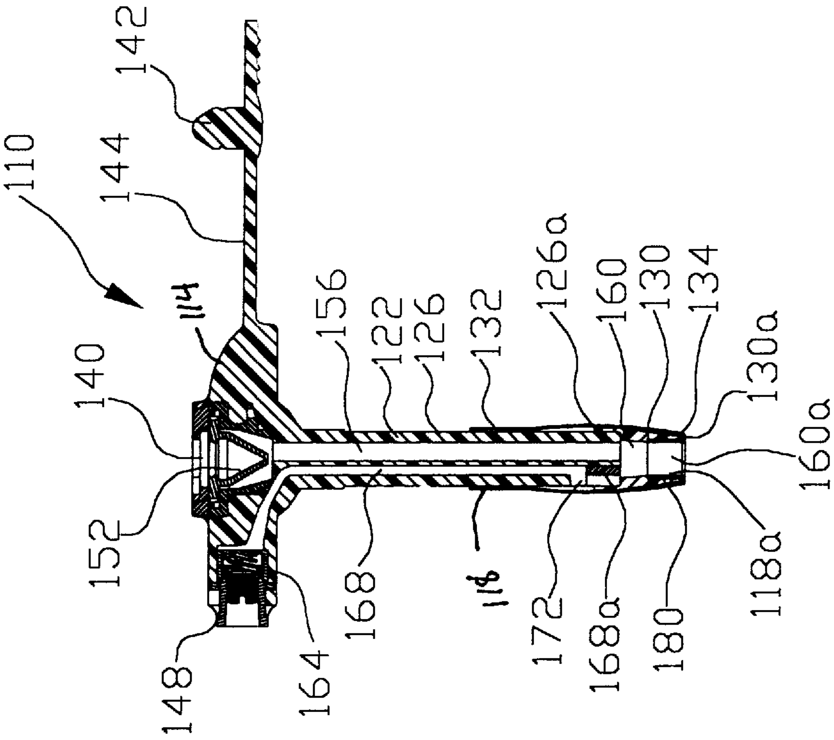
FIG. 3 shows a cross-sectional view of the balloon catheter of FIG. 2, taken along the longitudinal midline line A—A, with the uninflated balloon resting on the exterior of the catheter segment.

Turning now to FIG. 3, there is shown a cross-sectional view of the balloon catheter 110 of FIG. 2, taken along the longitudinal midline line A—A. The balloon catheter 110 includes the head 114, the balloon 118 and the catheter segment 122. As was mentioned previously, the head 114 includes a first, central opening 140 and a second, side opening 148. The first, central opening 140 includes an anti-reflux valve 152 which is configured to allow nutrient solutions, etc., to pass into the user, but to prevent the flow of fluids out of the user unless properly engaged by a syringe or other sampling device having a nipple which corresponds with the anti-reflux valve. The anti-reflux valve 152 is disposed in communication with a passageway in the form of a feeding lumen 156 which extends through the catheter shaft 126, and a passageway or channel 160 through the stiff tip 130 attached to the distal end 126*a* of the catheter shaft. When fluid is injected into the first, central opening 140, it flows through the anti-ref lux valve 152, the feeding lumen 156 and the channel 160 and into the user of the balloon catheter 110.

The second, side opening 148 forms an inflation port in which a releasable one-way valve 164 is disposed. The releasable one-way valve 164 is disposed in communication with an inflation lumen 168 which runs through the catheter shaft 126 substantially parallel to the feeding lumen 156. The distal end 168*a* of the inflation lumen 168 is plugged and a lateral opening 172 provided, so that the inflation lumen communicates with the elastomeric sleeve between cuffs 132 and 134, thereby forming the balloon 118. Application of fluid pressure (i.e. injection of air or saline solution) through the injection lumen 168 causes the fluid to fill the cavity between the elastomeric sleeve of the balloon 118 and the catheter segment 122, thereby causing the balloon to inflate.

Unlike the balloon catheter 10 shown in FIG. 1, the distal cuff 134 of the balloon 118 is not attached several millimeters from the distal end 130*a* and along the exterior of the stiff tip 130. Rather, the distal end 118*a* of the balloon 118 is wrapped over the distal end 130*a* of the stiff tip 130, and attached to an interior wall of the catheter segment 122 which forms the passageway through the catheter segment. Preferably, this is accomplished by attaching the distal end 118*a* of the balloon 118 to the interior of the stiff tip 130. In such a manner, the distal end 118*a* of the balloon 118 always covers the distal end 130*a* of the stiff tip 130. In other words, the distal end 118*a* of the balloon 118 prevents the stiff tip 130 from directly impacting anatomical structures disposed adjacent thereto.

An additional advantage of the configuration shown in FIGS. 2 through 5 is that the elastomeric sleeve which forms the balloon 118 is attached in such a way that no joint (such as joint 34*a* in FIG. 1) is formed at the proximal end of the balloon. As discussed in the background section, the joint 34*a* (FIG. 1) at the distal end of the balloon 18 in prior art configurations provides a edge upon which tissue around the stoma can catch, thereby interfering with insertion of the catheter 10. Additionally, the abrupt edge also provides yet another edge which is likely to cause irritation to anatomical structures which it repeatedly engages.

In contrast, the elastomeric sleeve which forms the balloon 118 in the present invention lacks any proximal joint which will interfere with insertion of the catheter, or which will cause irritation by repeated contact with anatomical structures. To the contrary, the proximal end of the elastomeric sleeve which forms the balloon 118 hugs the exterior of the catheter segment 122 and wraps around the distal end 130 of the stiff tip 130 rather than forming a joint. Thus, the elastomeric sleeve provides a smooth outer surface from the proximal cuff 132 to the distal end 130*a*, thereby further facilitating insertion of the catheter segment 122 through a stoma.

In a preferred embodiment, an annular recess 180 is formed in the stiff tip 130 adjacent the distal end 130*a* thereof. The annular recess 180 is preferably slightly greater in depth than the thickness of the distal end 118*a* of the balloon 118. The distal end 118*a* of the balloon 118 nests in the annular recess 180 and is attached thereto—preferably by an adhesive. Because the annular recess is slightly deeper than the thickness of the distal end 118*a* of the balloon 118, the distal end of the balloon forms a channel 160*a* which is approximately the same size in diameter as the channel 160 disposed proximal thereto through the stiff tip 130. In other words, the cuff 134 formed by bonding the distal end 118*a* of the balloon 118 into the annular recess 180 of the stiff tip 130 does not extend radially inward so as to potentially restrict fluid flow through the channel 160 and into the patient.

Figure 4:
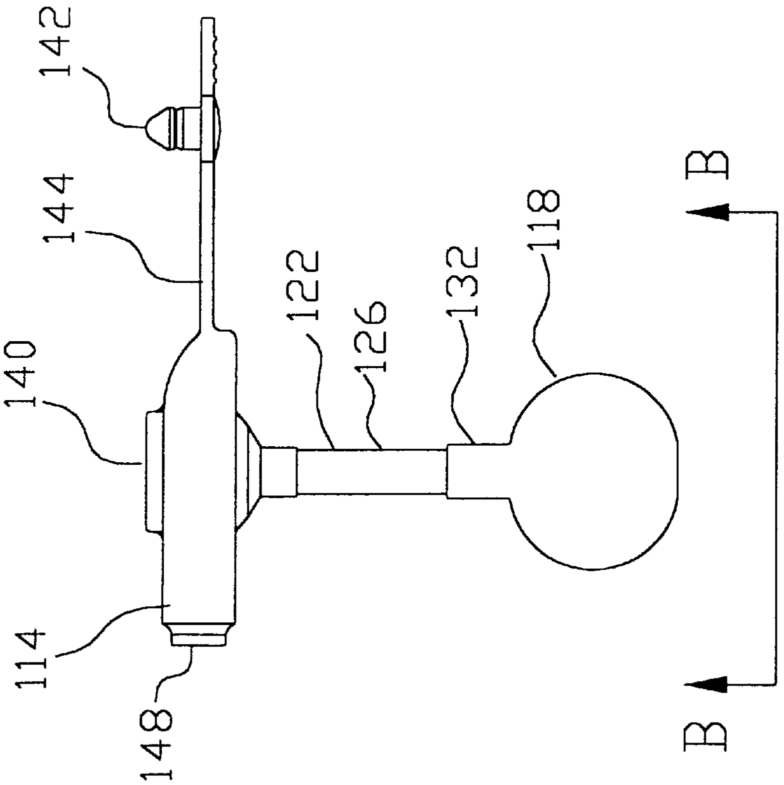
FIG. 4 shows a side view of the balloon catheter of FIG. 2, with the balloon in an inflated configuration.

Turning now to FIG. 4, there is shown a side view of the balloon catheter of FIG. 2, with the balloon in an inflated configuration. The head 114, the balloon 118, the catheter segment 122 and related structures are shown and marked in accordance with FIG. 2. FIG. 4 is provided to demonstrate the orientation of the balloon 118 when it is inflated. Unlike the prior art configuration shown in FIG. 1, the balloon 118 extends distally beyond the distal end 130*a* (FIG. 2) of the stiff tip 130 (FIG. 2). This, in turn, prevents the stiff tip 130 from directly contacting anatomical structures, such as opposing mucosa.

Figure 5:
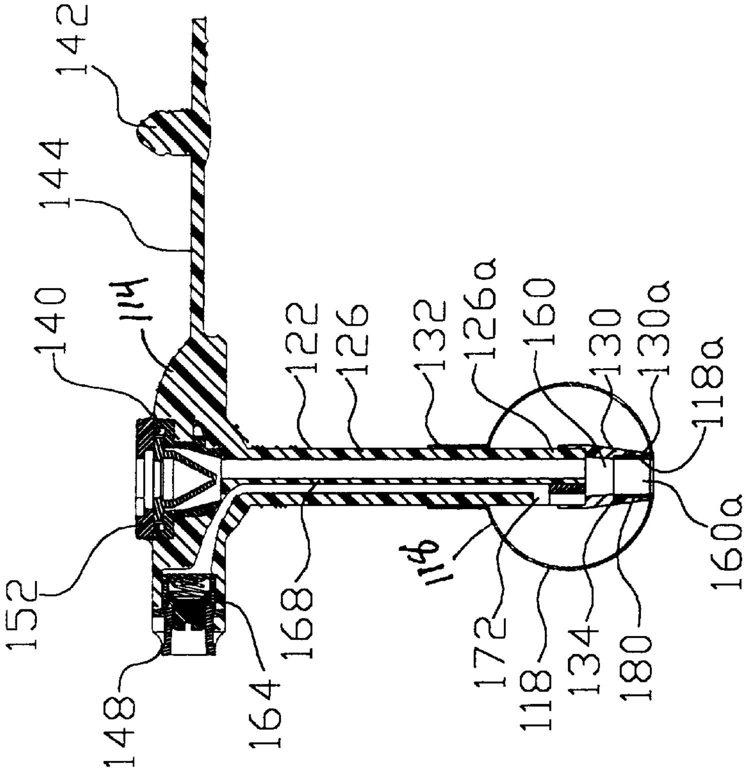
FIG. 5 shows a cross-sectional view of the balloon catheter of FIG. 4 taken along the longitudinal midline line B—B.

The view of FIG. 5 provides a better view of the significant advance obtained by the present invention by providing a cross-sectional view of the balloon catheter of FIG. 4 taken along the longitudinal midline line B—B. The view of the balloon catheter 110 is substantially the same as that of FIG. 2 (other than the inflation of the balloon 118), and is therefore numbered accordingly.

Focusing on the balloon 118 and the stiff tip 130, it will be apparent to those skilled in the art that the configuration described above provides a significant improvement in isolating the stiff tip from anatomical structures of the patient. Specifically, the formation of the distal cuff 134 (FIGS. 3 and 5) on the inside of the stiff tip 130 provides a direct barrier (the material forming the balloon) between the stiff tip and adjacent anatomical structures. Additionally, as the balloon 118 is inflated, the balloon extends a small distance distally before arching proximally toward the proximal cuff 132, thereby forming somewhat of a donut shape preventing forceful contact between the stiff tip 130 and any adjacent anatomical structures. Of course, the distance to which the balloon 118 extends distally of the stiff tip 130 will depend on a number of factors such as the flexibility of the material used in the balloon, the amount of material and whether any folds or other structural supports are provided along the balloon. When the balloon is deflated, the balloon 118 still prevents any direct contact between the stiff tip 130 and adjacent anatomical structures.

Another advantage of the present invention is that it allows a more secure distal seal without increasing the potential for irritation. Because the catheter segment of the prior art is unprotected at the distal end of the inflated balloon, it is desirable for minimizing discomfort to reduce the length of the cuff at the distal end of the catheter segment. If the cuff is too long, a considerable amount of the catheter segment would extend beyond the balloon. In contrast, by having the distal end 118*a* of the balloon 118 attach to the interior of the stiff tip 130, the distal end 130*a* of the stiff tip 130 is covered, and those making the balloon catheter 110 can form a much longer cuff to increase sealing without increasing irritation. The longer cuff provides an improved seal and thereby provides superior prevention of leaks from the balloon. While shown in FIGS. 3 and 5 as being disposed adjacent to the distal end of the stiff tip 130, the distal cuff 134 could be disposed further proximally within the catheter segment 122.

Thus, there is disclosed a balloon catheter with improved balloon orientation. Those skilled in the art will appreciate numerous modifications which can be made without departing from the scope and spirit of the present invention. For example, while the catheter shaft and the stiff tip are shown as two different elements which have been attached, it would be possible to form a catheter segment which utilizes a single piece of catheter tubing to perform the functions of the catheter shaft and the stiff tip. The appended claims are intended to cover such modifications.

What is claimed is:

1. A balloon catheter comprising:

an elongate catheter segment having a proximal end and a distal end; and an inflatable balloon attached to the elongate catheter tube adjacent the distal end so as to form a proximal cuff at a proximal end of the balloon and a distal cuff, the proximal cuff being attached to the exterior of the catheter segment and the distal cuff being attached to the interior of the catheter segment such that the balloon hugs the exterior of the catheter segment when not inflated, thereby facilitating insertion of the balloon catheter through a stoma.

2. The balloon catheter of claim 1, wherein the balloon has a distal end, wherein the catheter segment comprises a catheter shaft and a stiff tip attached to the catheter shaft, the stiff tip having an interior defining a passageway; and wherein the proximal end of the balloon is attached to the catheter shaft and the distal end of the balloon is attached to the interior of the stiff tip.

3. The balloon catheter according to claim 2, wherein the stiff tip has an annular recess, and wherein the distal end of the balloon nests in the recess.

4. The balloon according to claim 3, wherein the stiff tip has a distal end and wherein the annular recess is formed in the interior of the stiff tip immediately adjacent the distal end of the stiff tip.

5. The balloon according to claim 4, wherein the balloon is formed of an elastomeric sleeve having a thickness and wherein the annular recess is deeper than the thickness of the elastomeric sleeve.

6. The balloon catheter of claim 2, wherein the stiff tip has a channel extending therethrough, and wherein attachment of the distal end of the balloon to the stiff tip does not decrease the cross-sectional diameter of the channel extending through the stiff tip.

7. The balloon catheter of claim 2, wherein the balloon extends distally from the distal cuff, around the distal end of the stiff tip, and then proximally to the proximal cuff.

8. The balloon catheter of claim 1, wherein the catheter segment has a with a recess formed, and wherein the distal end of the balloon nests in the recess.

9. The balloon catheter of claim 1, wherein the balloon comprises an elastomeric sleeve having a proximal end and a distal end, and wherein the proximal cuff is formed at the proximal end of the elastomeric sleeve, and wherein the distal cuff is formed at the distal end of the elastomeric sleeve.

10. A balloon catheter comprising:

a head having at least two openings through which solution may be injected into a patient;

a catheter segment extending from the head, the catheter segment having a first and second lumen disposed in communication with the at least two openings; and a balloon formed by a sleeve with a first end attached to the exterior of the catheter segment so as to form a first cuff and a second end attached to the interior of the catheter segment so as to form a second cuff, the balloon collapsing on the catheter segment when not inflated to thereby facilitate insertion through a stoma.

11. The balloon catheter according to claim 10, wherein the first cuff is disposed proximally of the second cuff.

12. The balloon catheter according to claim 11, wherein the sleeve has a proximal end attached to the exterior of the catheter segment, and a distal end attached to the interior of the catheter segment.

13. The balloon catheter according to claim 12, wherein the catheter segment comprises a catheter shaft having a distal end and a stiff tip attached to the distal end of the catheter shaft.

14. The balloon catheter according to claim 13, wherein the proximal end of the sleeve is attached to the exterior of the catheter shaft, and wherein the distal end of the sleeve is attached to the interior of the stiff tip.

15. The balloon catheter according to claim 10, wherein the head has a plurality of valves configured for selectively controlling fluid flow through the balloon catheter.

16. The balloon catheter according to claim 10, wherein the head has a larger cross-sectional diameter than the catheter segment.

17. The balloon catheter according to claim 10, wherein the catheter segment has a distal tip and wherein the balloon covers said distal tip.

18. The balloon catheter according to claim 10, wherein the catheter segment has a distal tip, and wherein the balloon extends distally of the distal tip when inflated.

19. A balloon catheter configured for placement through a stoma into a body cavity so that the balloon catheter is maintained in the stoma, the balloon catheter comprising:

a head having at least one opening through which a fluid may be injected;

a catheter segment extending from the head portion to a distal tip, the catheter segment having an exterior and a wall defining a passageway through the interior; and an elongate sleeve attached to the exterior of the catheter segment and to the interior of the catheter segment about the passageway so as to form an inflatable balloon which covers the distal tip of the catheter segment, the sleeve being in collapsed state when not inflated wherein the sleeve closely surrounds the catheter segment, and wherein the sleeve extends radially outwardly from the catheter segment when inflated.

20. The balloon catheter according to claim 19, wherein the attachment of the elongate sleeve to the exterior of the catheter segment forms a proximal cuff of the balloon, and wherein the attachment of the elongate sleeve to the interior of the catheter segment forms a distal cuff of the balloon.

21. The balloon catheter according to claim 20, wherein the distal cuff defines a portion of the passageway through the catheter segment.

22. The balloon catheter according to claim 19, wherein the catheter segment comprises a catheter shaft and a stiff tip attached to a distal end of the catheter shaft, opposite the head.

23. The balloon catheter according to claim 22, wherein the sleeve is attached to the exterior of the catheter shaft and the interior of the stiff tip.

24. The balloon catheter according to claim 23, wherein the stiff tip comprises an annular recess, and wherein the sleeve is disposed in the annular recess.

25. The balloon catheter according to claim 19, wherein the attachment of the sleeve to the exterior of the catheter segment is proximal to the attachment of the sleeve to the interior of the catheter segment.

* * * * *

UNITED STATES PATENT AND TRADEMARK OFFICE

CERTIFICATE OF CORRECTION

PATENT NO. : 5,997,546

DATED : December 7, 1999

INVENTOR(S) : Mark Foster, Allan F. Willis, Kelly J. Christian

It is certified that error appears in the above-identified patent and that said Letters Patent is hereby corrected as shown below:

Column 7, claim 1, line 19, "adjacent the distal end of the balloon" should be inserted after "distal cuff"

Column 7, claim 8, line 52, "with a" should be deleted and "in the distal end" inserted after "formed".

Signed and Sealed this

Sixth Day of March, 2001

*Attest:*

Nicholas P. Godici

NICHOLAS P. GODICI

*Attesting Officer* *Acting Director of the United States Patent and Trademark Office*